United States Patent
Rao et al.

(10) Patent No.: US 10,851,352 B2
(45) Date of Patent: Dec. 1, 2020

(54) MYCOBACTERIUM NEOAURUM-DERIVED STEROID C27-MONOOXYGENASE AND APPLICATION THEREOF

(71) Applicant: Jiangnan University, Wuxi (CN)

(72) Inventors: Zhiming Rao, Wuxi (CN); Minglong Shao, Wuxi (CN); Xian Zhang, Wuxi (CN); Taowei Yang, Wuxi (CN); Meijuan Xu, Wuxi (CN)

(73) Assignee: JIANGNAN UNIVERSITY, Wuxi (CN)

(*) Notice: Subject to any disclaimer, the term of this patent is extended or adjusted under 35 U.S.C. 154(b) by 142 days.

(21) Appl. No.: 16/063,668

(22) PCT Filed: Aug. 29, 2016

(86) PCT No.: PCT/CN2016/097110
§ 371 (c)(1),
(2) Date: Jun. 18, 2018

(87) PCT Pub. No.: WO2018/028006
PCT Pub. Date: Feb. 15, 2018

(65) Prior Publication Data
US 2019/0153404 A1    May 23, 2019

(30) Foreign Application Priority Data
Aug. 10, 2016 (CN) .......................... 2016 1 0654331

(51) Int. Cl.
| | | |
|---|---|---|
| *C12N 1/21* | (2006.01) | |
| *C12N 15/53* | (2006.01) | |
| *C12N 9/02* | (2006.01) | |
| *C12N 15/67* | (2006.01) | |
| *C12P 33/16* | (2006.01) | |
| *C12P 33/00* | (2006.01) | |

(52) U.S. Cl.
CPC ............ *C12N 9/0073* (2013.01); *C12N 15/67* (2013.01); *C12P 33/00* (2013.01); *C12P 33/16* (2013.01); *C12Y 114/13072* (2013.01)

(58) Field of Classification Search
None
See application file for complete search history.

(56) References Cited

PUBLICATIONS

GenBank Accession No. WP_019510071 (Year: 2014).*

* cited by examiner

*Primary Examiner* — Rebecca E Prouty
(74) *Attorney, Agent, or Firm* — IPro, PLLC

(57) ABSTRACT

The present invention discloses a *Mycobacterium neoaurum*-derived steroid C27-monooxygenase and an application thereof, which belong to the technical fields of genetic engineering and enzyme engineering. By the method of gene knockout and intensive expression, the present invention screens out three isoenzymes of a key enzyme SMO in the process of degrading sterol side chains from *Mycobacterium neoaurum*. The three isoenzymes are intensively expressed respectively in the *Mycobacterium neoaurum* for the high yield of androsta-1,4-diene-3,17-dione (ADD), the yield of ADD is increased remarkably, wherein the effect of SMO2 is most remarkable. By overexpressing SMO2, the final ADD yield is increased from 5.2 g·L$^{-1}$ to 7.3 g·L$^{-1}$. The present invention provides a helpful guidance for the industrialization of the microbial fermentation method for increasing the ADD yield.

3 Claims, No Drawings
Specification includes a Sequence Listing.

SEQUENCE LISTING

```
<160> NUMBER OF SEQ ID NOS: 6

<210> SEQ ID NO 1
<211> LENGTH: 1275
<212> TYPE: DNA
<213> ORGANISM: Artificial Sequence
<220> FEATURE:
<223> OTHER INFORMATION: Synthetic DNA

<400> SEQUENCE: 1
atgaccgaca ccgcccacgc ccggcagccc aacattcctc ccggtttcga tttcaccgat      60
ccggacatct acgctcaccg gctgcccatc gaggaattcg ccgaaatgcg ccgggtggcg     120
cccatctggt ggaacgaaca accggcagaa aagggcggct cggcgatgg cgggtactgg      180 gtcgtcacca agcacagaga cgtcaaggag gtttcgcggc gcagcgacgt cttctccagc     240 ctgccaaga ccgcgctgcc gcgttatgcc gacggcacgg tcaaggaaca gatcgacaca     300
ggcaagttcg tcctgctgaa catggacgcc ccgcatcaca cccacctgcg caagatcatc     360
tcccgcgcct tcactccgcg cgccatcgag ctgttgcgcg cagacctggc cgaacgggcc     420
cgcgagatcg ctgccagggc ggccgcggcc gggtcgggcg atttcgtcga acaggtgtcc     480
tgcgaattgc cgctgcaggc catcgccggg ctgatgggtg ttcctcagga agaccggatg     540
aagctgttcc actggtccaa ccagatggtc ggcgacatgg accccgagtt cgccggtaac     600
gacgccatca gcgcgtcggt cgagctgatc acctatggca tgaagctggc cgccgaacgc     660
gccgactccc ccggtgagga cctggtcacc aagctggtgc aggccgatgt cgaggggcac     720
aagctcaccg acgacgaact cgggttcttc gtggttctgt tcgccgttgc gggtaacgag     780
acgacgcgca actcgatcac ccaggggatg atggcgttca ccgacttccc ggatcagtgg     840
gagctgttca gcgggagcg gccgtcgacg acggccgacg agatcgtccg gtgggccaca     900
ccggtgacat cgtttcagcg caccgctctc gccgacaccg aactgtccgg ggtgtcgatc     960
aaaaagggtc agcgcgtggt gatgatgtac cgcgcagcca atttcgacga ggatgttttc    1020
gaggatccgt acacgttcga catcctgcgt gacccgaacc cccatgtcgg cttcggcggc    1080
accggggcgc attactgcat cggcaccagc ctcgcccgga tgaccatcga tctgatgttc    1140
aacgcgatcg ccgacgcgat gcccgacatc acctcgctgg cccagcccga acggttgcgg    1200
tccggctggc tcaatggcat caaacactgg caggtcgact acgtgggcgc gtcgaaacag    1260
gctgtgcacc actag                                                     1275

<210> SEQ ID NO 2
<211> LENGTH: 1236
<212> TYPE: DNA
<213> ORGANISM: Artificial Sequence
```

```
<220> FEATURE:
<223> OTHER INFORMATION: Synthetic DNA

<400> SEQUENCE: 2
atgacgacga tggatgcgtg tccgttcggt gcggggtacg acttcaccga ccccgaggtg      60
ctgctgcagg ggcttccggt cacggagttc gcccacctgc gcaagaccgc accgatctgg     120
tggaacgccc agggtgagtc gatcttcgat gacggcggct attgggtgat cagccggcac     180
gaagacgtca agaccatctc ccgcaactcc cgcgacatct ggtccaccaa tgccaaggga     240
gcggtcatgc ggctgcccga cggcatcacc gccgaccaac tcgatctgac caaggccctg     300
ctgatcaatc acgacgcccc ggagcacacc cggctgcgca agctggtctc gcgcctgttc     360
acgccgcgct cggtggccgc gctcgaggag aagctggcgg tggcggcacg cgagatcgtg     420
gcacgggccg ccgaacgcgg ctccggcaat ttcgtcgatg acgtggcgat gccgctgccg     480
ctacaggcca tcgccgacct gatcggggtg cccgaggcgg accgggagaa gatattccac     540
tggtcgaact gcatcatgaa caccgacgac cccgatttcg acagcgaccc gacgaccgcc     600
aacgcggagc tgatgggtta cgcctacaac atggccgaac aacgccggaa gtgcccggcc     660
gatgacatcg tcacccgcct ggtccaggcc gatctgggcg gagaagaggg catcaccgaa     720
gtggagttcg ccttcttcgt gatcctgctg gccgtggcag gcaatgagac cacccgcaat     780
acgatgaccc acgggatgaa cgccttcctc gaaaacccgg atcaatggga acttttcaag     840
cgtgagcgcc ccgataccgc catcgaggag atcatccggt gggccagccc ggtgcactgc     900
ttccagcgca cggcgctcca ggacaccgag atcggcgggg tcaccatcaa gcaaggccag     960
cgggtcgggc tgttctacag ctcggcaaac tacgacgaat ccgtgttcac cgacccgttc    1020
cggttcgaca tcctgcgcaa cccgaatccg catctggcct tcggtggcaa cggcgcacat    1080
ttctgcatcg gcgccaacct ggcccgcatg agatcaagc tgatgttcaa cgagatcgcc    1140
aaccagatcc cggacatctc caaactggct gaaccgcagc gccttcgatc cggctggatc    1200
aacggcgtga aggaactgca ggtttcctac tcctga                             1236

<210> SEQ ID NO 3
<211> LENGTH: 1254
<212> TYPE: DNA
<213> ORGANISM: Artificial Sequence
<220> FEATURE:
<223> OTHER INFORMATION: Synthetic DNA

<400> SEQUENCE: 3
atgcccagcc ccaacctgcc caagggcttc gacccgctgg acgccagtct gaacctcgaa      60
cgcctgcccg tggaggagtt ggcggagatt cgccgcgccg agcccgtcca ctgggtggac     120
gtgccggaag ggaccggggg cttcggcgac aagggctact ggatcgtcac caagcatgcc     180
gacgtcaaag aggtctcgaa gcgaaacgac atcttcggca gctcacccga cggcgccatc     240
ccggtctggc cgcaggagat gacccgcgac gccatcgatc tgcagaaggc cgtcctgctc     300
aacatggacg cgccgcagca cacccggttg cgcaagatca tctcgcgcgg gttcaccccg     360
cgcgccatcg gacggctcga agacgagttg cgggcccgtg cccgcaagat cgccgaaacc     420
gcggcggcag ccgttcgggg cgacttcgtc gagcaggtgt cctgcgaact gccgctgcag     480
gccatcgccg aactgctcgg tgtgccgcag gacgaccggg acaagatctt ccgctggtcc     540
aatgagatga ctgcgggcga ggaccccgag tacgccgatg tcgatccggc gatgtcctcc     600
ttcgagctca tcacctacgc catgaagatg gccgaggagc gggcgcagaa cccgaccgag     660
```

-continued

```
gacatcgtga ccaagctgat cgaggccgat atcgagggcg agaagctctc tgacgacgag    720
ttcggtttct tcgtggtcat gcttgccgtc gcaggcaacg agaccacccg caactcgatc    780
acccacggca tgatcgcctt cgccgacaat cccgaccagt gggagctcta caagaaggaa    840
cgcccgggca cgccgccga cgagatcatc cgttgggcga caccggtgtc ggcgttccag      900
cgcacggcac tggaggacac cgagctcgcc ggggcgaaga tcaagaaggg cgatcgtgtg    960
gtgatgtcct accgcgccgc caacttcgac gacgaggcgt tcgacaaccc gcaccagttc   1020
aacatcctgc gtgatcccaa cccgcacgtc ggattcggtg gtaccggtgc gcactactgt   1080
atcggcgcaa acctggcccg catgaccatc aacctgatct tcaacgcgat cgccgacgtg   1140
atgcccgaca tcacaccgat cggcgagccg gagcggttga agtccggctg gctcaacgga   1200
atcaagcact ggcaggtcga ctacaccggc gcgggcgccg cgcctcgag ctag          1254
```

<210> SEQ ID NO 4
<211> LENGTH: 424
<212> TYPE: PRT
<213> ORGANISM: Artificial Sequence
<220> FEATURE:
<223> OTHER INFORMATION: Protein translated from Synthetic DNA

<400> SEQUENCE: 4

```
Met Thr Asp Thr Ala His Ala Arg Gln Pro Asn Ile Pro Pro Gly Phe
1               5                   10                  15

Asp Phe Thr Asp Pro Asp Ile Tyr Ala His Arg Leu Pro Ile Glu Glu
                20                  25                  30

Phe Ala Glu Met Arg Arg Val Ala Pro Ile Trp Trp Asn Glu Gln Pro
            35                  40                  45

Ala Glu Lys Gly Gly Phe Gly Asp Gly Gly Tyr Trp Val Val Thr Lys
        50                  55                  60

His Arg Asp Val Lys Glu Val Ser Arg Arg Ser Asp Val Phe Ser Ser
65                  70                  75                  80

Leu Ala Lys Thr Ala Leu Pro Arg Tyr Ala Asp Gly Thr Val Lys Glu
                85                  90                  95

Gln Ile Asp Thr Gly Lys Phe Val Leu Leu Asn Met Asp Ala Pro His
            100                 105                 110

His Thr His Leu Arg Lys Ile Ile Ser Arg Ala Phe Thr Pro Arg Ala
        115                 120                 125

Ile Glu Leu Leu Arg Ala Asp Leu Ala Glu Arg Ala Arg Glu Ile Ala
130                 135                 140

Ala Arg Ala Ala Ala Gly Ser Gly Asp Phe Val Glu Gln Val Ser
145                 150                 155                 160

Cys Glu Leu Pro Leu Gln Ala Ile Ala Gly Leu Met Gly Val Pro Gln
                165                 170                 175

Glu Asp Arg Met Lys Leu Phe His Trp Ser Asn Gln Met Val Gly Asp
            180                 185                 190

Met Asp Pro Glu Phe Ala Gly Asn Asp Ala Ile Ser Ala Ser Val Glu
        195                 200                 205

Leu Ile Thr Tyr Gly Met Lys Leu Ala Ala Glu Arg Ala Asp Ser Pro
    210                 215                 220

Gly Glu Asp Leu Val Thr Lys Leu Val Gln Ala Asp Val Glu Gly His
225                 230                 235                 240

Lys Leu Thr Asp Asp Glu Leu Gly Phe Phe Val Val Leu Leu Ala Val
                245                 250                 255

Ala Gly Asn Glu Thr Thr Arg Asn Ser Ile Thr Gln Gly Met Met Ala
```

-continued

```
                260                 265                 270
Phe Thr Asp Phe Pro Asp Gln Trp Glu Leu Phe Lys Arg Glu Arg Pro
            275                 280                 285
Ser Thr Thr Ala Asp Glu Ile Val Arg Trp Ala Thr Pro Val Thr Ser
        290                 295                 300
Phe Gln Arg Thr Ala Leu Ala Asp Thr Glu Leu Ser Gly Val Ser Ile
305                 310                 315                 320
Lys Lys Gly Gln Arg Val Val Met Met Tyr Arg Ala Ala Asn Phe Asp
                325                 330                 335
Glu Asp Val Phe Glu Asp Pro Tyr Thr Phe Asp Ile Leu Arg Asp Pro
            340                 345                 350
Asn Pro His Val Gly Phe Gly Gly Thr Gly Ala His Tyr Cys Ile Gly
        355                 360                 365
Thr Ser Leu Ala Arg Met Thr Ile Asp Leu Met Phe Asn Ala Ile Ala
        370                 375                 380
Asp Ala Met Pro Asp Ile Thr Ser Leu Ala Gln Pro Glu Arg Leu Arg
385                 390                 395                 400
Ser Gly Trp Leu Asn Gly Ile Lys His Trp Gln Val Asp Tyr Val Gly
                405                 410                 415
Ala Ser Lys Gln Ala Val His His
            420

<210> SEQ ID NO 5
<211> LENGTH: 411
<212> TYPE: PRT
<213> ORGANISM: Artificial Sequence
<220> FEATURE:
<223> OTHER INFORMATION: Protein translated from Synthetic DNA

<400> SEQUENCE: 5

Met Thr Thr Met Asp Ala Cys Pro Phe Gly Ala Gly Tyr Asp Phe Thr
1               5                   10                  15
Asp Pro Glu Val Leu Leu Gln Gly Leu Pro Val Thr Glu Phe Ala His
                20                  25                  30
Leu Arg Lys Thr Ala Pro Ile Trp Trp Asn Ala Gln Gly Glu Ser Ile
            35                  40                  45
Phe Asp Asp Gly Gly Tyr Trp Val Ile Ser Arg His Glu Asp Val Lys
        50                  55                  60
Thr Ile Ser Arg Asn Ser Arg Asp Ile Trp Ser Thr Asn Ala Lys Gly
65                  70                  75                  80
Ala Val Met Arg Leu Pro Asp Gly Ile Thr Ala Asp Gln Leu Asp Leu
                85                  90                  95
Thr Lys Ala Leu Leu Ile Asn His Asp Ala Pro Glu His Thr Arg Leu
            100                 105                 110
Arg Lys Leu Val Ser Arg Leu Phe Thr Pro Arg Ser Val Ala Ala Leu
        115                 120                 125
Glu Glu Lys Leu Ala Val Ala Ala Arg Glu Ile Val Ala Arg Ala Ala
    130                 135                 140
Glu Arg Gly Ser Gly Asn Phe Val Asp Val Ala Met Pro Leu Pro
145                 150                 155                 160
Leu Gln Ala Ile Ala Asp Leu Ile Gly Val Pro Glu Ala Asp Arg Glu
                165                 170                 175
Lys Ile Phe His Trp Ser Asn Cys Ile Met Asn Thr Asp Asp Pro Asp
            180                 185                 190
Phe Asp Ser Asp Pro Thr Thr Ala Asn Ala Glu Leu Met Gly Tyr Ala
```

```
                    195                 200                 205
Tyr Asn Met Ala Glu Gln Arg Arg Lys Cys Pro Ala Asp Asp Ile Val
            210                 215                 220

Thr Arg Leu Val Gln Ala Asp Leu Gly Gly Glu Gly Ile Thr Glu
225                 230                 235                 240

Val Glu Phe Ala Phe Val Ile Leu Leu Ala Val Ala Gly Asn Glu
                    245                 250                 255

Thr Thr Arg Asn Thr Met Thr His Gly Met Asn Ala Phe Leu Glu Asn
            260                 265                 270

Pro Asp Gln Trp Glu Leu Phe Lys Arg Glu Arg Pro Asp Thr Ala Ile
            275                 280                 285

Glu Glu Ile Ile Arg Trp Ala Ser Pro Val His Cys Phe Gln Arg Thr
290                 295                 300

Ala Leu Gln Asp Thr Glu Ile Gly Gly Val Thr Ile Lys Gln Gly Gln
305                 310                 315                 320

Arg Val Gly Leu Phe Tyr Ser Ser Ala Asn Tyr Asp Glu Ser Val Phe
                    325                 330                 335

Thr Asp Pro Phe Arg Phe Asp Ile Leu Arg Asn Pro Asn Pro His Leu
            340                 345                 350

Ala Phe Gly Gly Asn Gly Ala His Phe Cys Ile Gly Ala Asn Leu Ala
                    355                 360                 365

Arg Met Glu Ile Lys Leu Met Phe Asn Glu Ile Ala Asn Gln Ile Pro
370                 375                 380

Asp Ile Ser Lys Leu Ala Glu Pro Gln Arg Leu Arg Ser Gly Trp Ile
385                 390                 395                 400

Asn Gly Val Lys Glu Leu Gln Val Ser Tyr Ser
                    405                 410

<210> SEQ ID NO 6
<211> LENGTH: 417
<212> TYPE: PRT
<213> ORGANISM: Artificial Sequence
<220> FEATURE:
<223> OTHER INFORMATION: Protein translated from Synthetic DNA

<400> SEQUENCE: 6

Met Pro Ser Pro Asn Leu Pro Lys Gly Phe Asp Pro Leu Asp Ala Ser
1               5                   10                  15

Leu Asn Leu Glu Arg Leu Pro Val Glu Glu Leu Ala Glu Ile Arg Arg
                20                  25                  30

Ala Glu Pro Val His Trp Val Asp Val Pro Glu Gly Thr Gly Gly Phe
            35                  40                  45

Gly Asp Lys Gly Tyr Trp Ile Val Thr Lys His Ala Asp Val Lys Glu
        50                  55                  60

Val Ser Lys Arg Asn Asp Ile Phe Gly Ser Ser Pro Asp Gly Ala Ile
65                  70                  75                  80

Pro Val Trp Pro Gln Glu Met Thr Arg Asp Ala Ile Asp Leu Gln Lys
                85                  90                  95

Ala Val Leu Leu Asn Met Asp Ala Pro Gln His Thr Arg Leu Arg Lys
            100                 105                 110

Ile Ile Ser Arg Gly Phe Thr Pro Arg Ala Ile Gly Leu Glu Asp
        115                 120                 125

Glu Leu Arg Ala Arg Ala Arg Lys Ile Ala Glu Thr Ala Ala Ala
130                 135                 140

Gly Ser Gly Asp Phe Val Glu Gln Val Ser Cys Glu Leu Pro Leu Gln
```

-continued

```
145                 150                 155                 160
Ala Ile Ala Glu Leu Leu Gly Val Pro Gln Asp Asp Arg Asp Lys Ile
                165                 170                 175
Phe Arg Trp Ser Asn Glu Met Thr Ala Gly Glu Asp Pro Glu Tyr Ala
                180                 185                 190
Asp Val Asp Pro Ala Met Ser Ser Phe Glu Leu Ile Thr Tyr Ala Met
            195                 200                 205
Lys Met Ala Glu Glu Arg Ala Gln Asn Pro Thr Glu Asp Ile Val Thr
        210                 215                 220
Lys Leu Ile Glu Ala Asp Ile Glu Gly Glu Lys Leu Ser Asp Asp Glu
225                 230                 235                 240
Phe Gly Phe Phe Val Val Met Leu Ala Val Ala Gly Asn Glu Thr Thr
                245                 250                 255
Arg Asn Ser Ile Thr His Gly Met Ile Ala Phe Ala Asp Asn Pro Asp
                260                 265                 270
Gln Trp Glu Leu Tyr Lys Lys Glu Arg Pro Gly Thr Ala Ala Asp Glu
                275                 280                 285
Ile Ile Arg Trp Ala Thr Pro Val Ser Ala Phe Gln Arg Thr Ala Leu
        290                 295                 300
Glu Asp Thr Glu Leu Ala Gly Ala Lys Ile Lys Lys Gly Asp Arg Val
305                 310                 315                 320
Val Met Ser Tyr Arg Ala Ala Asn Phe Asp Asp Glu Ala Phe Asp Asn
                325                 330                 335
Pro His Gln Phe Asn Ile Leu Arg Asp Pro Asn Pro His Val Gly Phe
                340                 345                 350
Gly Gly Thr Gly Ala His Tyr Cys Ile Gly Ala Asn Leu Ala Arg Met
                355                 360                 365
Thr Ile Asn Leu Ile Phe Asn Ala Ile Ala Asp Val Met Pro Asp Ile
        370                 375                 380
Thr Pro Ile Gly Glu Pro Glu Arg Leu Lys Ser Gly Trp Leu Asn Gly
385                 390                 395                 400
Ile Lys His Trp Gln Val Asp Tyr Thr Gly Ala Gly Ala Gly Ala Ser
                405                 410                 415
Ser
```

US 10,851,352 B2

MYCOBACTERIUM NEOAURUM-DERIVED STEROID C27-MONOOXYGENASE AND APPLICATION THEREOF

TECHNICAL FIELD

The disclosure herein relates to the field of genetic engineering and enzyme engineering, and more particularly relates to a *mycobacterium neoaurum*-derived steroid C27-monooxygenase and an application thereof.

BACKGROUND

Because of a variety of physiological functions, steroid hormone drugs play a very important role in regulating the body, and therefore have been widely applied clinically. Steroid hormone drugs have been used widely to resist tumors, inflammation, bacteria, viruses, hormones, allergy, etc. In addition, various sex hormone drugs are main drugs for treating sexual organ degradation and gynecological diseases, and are main ingredients of oral contraceptives. Moreover, steroid hormone drugs can also serve as active ingredients of anti-obesity drugs for preventing coronary heart disease, and as HIV integrase inhibitors for preventing HIV infection and treating AIDS, etc. As important intermediates of the steroid hormone drugs, androsta-4-ene-3,17-dione (AD) and androsta-1,4-diene-3,17-dione (ADD) can almost synthesize all steroid hormone drugs, and play an important role in the industrialized production of steroids.

At present, there are two main approaches to the preparation of AD and ADD: in one approach, diosgenin is extracted from wide Chinese herbal medicine plants, such as Dioscorea Zingiberensis C. H. Wright and Dioscorea althaeoides R. Knuth, and chemical synthesis is then carried out. However, this approach has the problems of high production cost, complex process, severe environment pollution, etc; in the other approach, with zoosterol and phytosterol existing abundantly in nature as materials, by means of the microbial fermentation technique, sterol side chains are degraded selectively, and thereby a target product is obtained. The microbial method has the advantages of low cost, environment-friendliness, etc., and is more and more valued by people. At present, when conducting steroid drug preparation, the advanced countries in the world mostly adopt the zoosterol and the phytosterol as starting materials to carry out microbial transformation, and obtain steroid drug intermediates before proceeding with preparation.

Many scholars have conducted a lot of researches on the synthesis of AD/ADD by the microbial transformation of sterols, wherein mycobacteria are one of excellent strains for the production of AD/ADD. It has been reported that the metabolic pathway of the synthesis of AD/ADD by the microbial transformation of sterols requires a large number of enzymes, but which enzymes participate have not yet been thoroughly determined in researches. The progress of current researches is that only the enzyme in the first step of sterol transformation, which is cholesterol oxidase, and the enzyme in the last step, which is 3-ketosteroid-$\Delta^1$-dehydrogenase, have been identified and proved. Other enzymes in the approach have not yet been identified and applied.

Therefore, it is necessary to make in-depth research on key enzymes in the process of synthesizing AD/ADD by utilizing mycobacteria to transform sterols and the identification of their functions in order to develop a method capable of promoting mycobacteria to transform sterols to synthesize AD/ADD on this basis.

SUMMARY

In order to solve the above-mentioned problem, by the method of gene knockout and complementation, the present invention has screened out three isoenzymes (SMO1, SMO2, SMO3) of steroid C27-monooxygenase (SMO) as a key enzyme in the process of degrading sterol side chains from *Mycobacterium neoaurum* for the first time. By respectively intensively expressing the three isoenzymes in the *Mycobacterium neoaurum* for the high yield of androsta-1,4-diene-3,17-dione (ADD), ADD yields are all increased obviously, wherein the effect of the intensive expression of SMO2 in increasing the yield of ADD is more remarkable. Both the function identification and application of the steroid C27-monooxygenase in the *mycobacterium neoaurum* are reported for the first time, and recombinant bacteria can significantly increase the yield of ADD. The final ADD yield of the strain intensively expressing the gene SMO2 is increased from 5.2 g·L$^{-1}$ to 7.3 g·L$^{-1}$.

The first objective of the present invention is to provide a steroid C27-monooxygenase, and the amino acid sequence of the steroid C27-monooxygenase is shown as SEQ ID NO. 4, SEQ ID NO. 5 or SEQ ID NO. 6.

The second objective of the present invention is to provide a recombinant *Mycobacterium neoaurum* for increasing the yield of ADD, and the recombinant bacteria are *Mycobacterium neoaurum* overexpressing a steroid C27-monooxygenase gene; and the steroid C27-monooxygenase gene is any one or two or more of genes Smo1, Smo2 and Smo3.

In one embodiment of the present invention, the amino acid sequence of the steroid C27-monooxygenase gene Smo1 is shown as SEQ ID NO. 4, and the nucleotide sequence is shown as SEQ ID NO. 1.

In one embodiment of the present invention, the amino acid sequence of the steroid C27-monooxygenase gene Smog is shown as SEQ ID NO. 5, and the nucleotide sequence is shown as SEQ ID NO. 2.

In one embodiment of the present invention, the amino acid sequence of the steroid C27-monooxygenase gene Smo3 is shown as SEQ ID NO. 6, and the nucleotide sequence is shown as SEQ ID NO. 3.

In one embodiment of the present invention, the recombinant *Mycobacterium neoaurum* overexpresses the steroid C27-monooxygenase genes with *Mycobacterium neoaurum* as an original strain.

In one embodiment of the present invention, the original strain can be any one of the following strains: *Mycobacterium neoaurum* ATCC 25795, *Mycobacterium neoaurum* ZJUVN (CGMCC 5477), *Mycobacterium neoaurum* NwIB-01 (CCTCC M 209094), *Gordonia neofelifaecis* NRRL B-59395 (CCTCC AB-209144), *Arthrobacter simplex* (TCCC 11037), *Mycobacterium fortuitum* subsp. *fortuitum* (MTCC 929) or *Mycobacterium neoaurum* JC-12.

*Mycobacterium neoaurum* ATCC 25795 has been disclosed by Yao K, Ku L-Q, Wang F-Q, Wei D-Z (2014) in the document of Characterization and engineering of 3-ketosteroid-Δ1-dehydrogenase and 3-ketosteroid-9α-hydroxylase in *Mycobacterium neoaurum* ATCC 25795 to produce 9α-hydroxy-4-androstene-3,17-dione through the catabolism of sterols. Metab Eng 24(0):181-191 doi:http://dx.doi.org/10.1016/j.ymben.2014.05.005.

*Mycobacterium neoaurum* ZJUVN (CGMCC 5477) has been disclosed by Zhang X-y, Peng Y, Su Z-r, Chen Q-h, Ruan H, He G-q (2013) in the document of Optimization of biotransformation from phytosterol to androstenedione by a mutant *Mycobacterium neoaurum* ZJUVN-08. Journal of Zhejiang University SCIENCE B 14(2):132-143 doi: 10.1631/jzus.B1200067.

*Mycobacterium neoaurum* NwIB-01 (CCTCC M 209094) has been disclosed by Wei W, Fan S-Y, Wang F-Q, Wei D-Z (2014) in the document of Accumulation of androstadienedione by overexpression of heterologous 3-ketosteroid Δ1-dehydrogenase in *Mycobacterium neoaurum* NwIB-01. World J Microbiol Biotechnol 30(7):1947-1954 doi: 10.1007/s11274-014-1614-3.

*Gordonia neofelifaecis* NRRL B-59395 (CCTCC AB-209144) has been disclosed by Liu Y, Chen G, Ge F, Li W, Zeng L, Cao W (2011) in the document of Efficient biotransformation of cholesterol to androsta-1,4-diene-3,17-dione by a newly isolated actinomycete *Gordonia neofelifaecis*. World J Microbiol Biotechnol 27(4):759-765 doi: 10.1007/s11274-010-0513-5.

*Arthrobacter simplex* (TCCC 11037) has been disclosed by Wang M, Zhang L T, Shen Y B, Ma Y H, Zheng Y, Luo J M (2009) in the document of Effects of hydroxypropyl-β-cyclodextrin on steroids 1-en-dehydrogenation biotransformation by *Arthrobacter simplex* TCCC 11037. J Mol Catal, B Enzym 59(1-3):58-63 doi:hp:// dx.doi.org/10.1016/j.molcatb.2008.12.017.

*Mycobacterium fortuitum* subsp. *fortuitum* (MTCC 929) has been disclosed by Galla V, Banerjee T, Patil S (2010) in the document of Bioconversion of soysterols to androstenedione by *Mycobacterium fortuitum* subsp. *fortuitum* NCIM 5239, a mutant derived from total sterol degrader strain. J Chem Technol Biotechnol 85(8):1135-1141 doi:10.1002/jctb.2410.

*Mycobacterium neoaurum* JC-12 has been disclosed by Shao M L, Zhang X, Rao Z M, Xu M J, Yang T W, Li H, Xu Z H (2015) in the document of Enhanced production of androsta-1,4-diene-3,17-dione by *Mycobacterium neoaurum* JC-12 using three-stage fermentation strategy. PLoS ONE 10(9): e0137658.

In one embodiment of the present invention, with regard to overexpression, specifically, the steroid C27-monooxygenase genes are connected to a plasmid pMV261, so that recombinant plasmids are obtained, and the recombinant plasmids are then transformed into the original strain.

The third objective of the present invention is to provide a method for increasing the yield of ADD by overexpressing a steroid C27-monooxygenase gene, the method utilizes the recombinant *Mycobacterium neoaurum* disclosed by the present invention as a production strain to fermentatively produce ADD; the recombinant *Mycobacterium neoaurum* overexpresses the steroid C27-monooxygenase gene; and the steroid C27-monooxygenase gene is any one or two or more of genes Smo1, Smo2 and Smo3.

In one embodiment of the present invention, the amino acid sequence of the steroid C27-monooxygenase gene is shown as SEQ ID NO.4, SEQ ID NO.5 or SEQ ID NO.6.

In one embodiment of the present invention, fermentative production adopts phytosterol or/and cholesterol as a substrate.

In one embodiment of the present invention, the ingredients of a fermentation medium for fermentation are: 20 g·L$^{-1}$ cholesterol, 20 g·L$^{-1}$ glucose, 10 g·L$^{-1}$ peptone, 6 g·L$^{-1}$ beef extract, 3 g·L$^{-1}$ K$_2$HPO$_4$, 0.5 g·L$^{-1}$ MgSO$_4$·7H$_2$O, 5×10$^{-4}$ g·L$^{-1}$ MnCl$_2$·4H$_2$O and 60 g·L$^{-1}$ hydroxypropyl-β-cyclodextrin, and pH is 7.5.

In one embodiment of the present invention, in fermentative production, fermentation is carried out under the conditions of 30° C. and 160 rpm for 168 h.

The fourth objective of the present invention is to provide ADD produced from the recombinant bacteria.

The fifth objective of the present invention is to provide an application of the recombinant bacteria or the steroid C27-monooxygenase genes in the preparation of a drug.

In one embodiment of the present invention, the drug is an anti-tumor, anti-inflammation, antibacterial, antiviral, anti-hormone or antiallergic drug.

In one embodiment of the present invention, the drug is a drug for treating sexual organ degeneration, a drug for gynecological diseases, an anti-obesity drug, a drug for preventing coronary heart disease, an HIV integrase inhibitor or etc.

(1) The present invention screens out the three isoenzyme genes of the steroid C27-monooxygenase in the *mycobacterium neoaurum* by a genetic engineering means, and identifies the enzymes in the second step of the sterol transformation process based on the steroid C27-monooxygenase (SMO) by means of the method of gene knockout and knocked-out gene complementation. The present invention proves the functions of the three isoenzymes in the process of sterol metabolism, determines their key role in the process of sterol transformation, and verifies they are key enzymes in the process of synthesizing AD/ADD by utilizing mycobacteria to transform sterols.

(2) On the basis of determining the key enzymes, the present invention applies them in the process of synthesizing AD/ADD by sterol transformation in order to increase the yield of ADD, and has discovered that the effect of SMO2 in increasing the yield of ADD is most remarkable. Ultimately, by overexpressing SMO2, the yield of ADD is increased from 5.2 g·L$^{-1}$ to 7.3 g·L$^{-1}$, increased by 40.4 percent in comparison with the original bacteria. The present invention provides a helpful guidance for the industrialization of the microbial fermentation method for increasing the yield of ADD.

DETAILED DESCRIPTION

Main reagents: Phytosterol (soyasterol≥95%) was purchased from Lilly Biotechnology (Huzhou) Co., Ltd, and ADD was purchased from American SIGMA company.

HPLC analysis of ADD: ADD had characteristic absorption peaks under an ultraviolet wavelength of 254 nm, so the HPLC method was adopted to determine product concentration. Chromatographic conditions: chromatographic column: DimosoilC18 (5 μl, 250 mm×4.6 mm); mobile phase: methanol-water (V/V=70:30); detector: UV Detector; detection wavelength: 254 nm; column temperature: 30° C.; sample amount: 104; and flow velocity: 1.0 ml·min$^{-1}$.

Example 1: Construction of SMO Knockout Strains and Corresponding Complementation Strains By querying the whole genome information of *Mycobacterium neoaurum*, three SMO isoenzymes were screened out. With the *Mycobacterium neoaurum* with SMO enzyme activity in a lab as an original strain and its chromosome as a template, the PCR measure was utilized to obtain the genes of the three enzymes. By means of the design of gene knockout primers, the PCR measure was utilized to obtain knocked-out genes, which were connected to a *Mycobacterium* knockout plasmid p2NIL, so that knockout plasmids were constructed, and after the construction was verified successful by PCR, the knockout plasmids were transformed into the *Mycobacterium neoaurum*. With cholest-4-en-3-one as a substrate, the degradation of the substrate by knockout strains was tested. On the basis of the knockout strains, knocked-out gene complementation strains were constructed, that was, by designing primers, the PCR measure was utilized to amplify complete SMO genes, which were connected to an integration vector pMV306, so that integrative plasmids were constructed, and after the construction was verified successful by PCR, the integrative plasmids were transformed into the corresponding knockout strains, so that the knocked-out gene complementation strains were constructed; and under the same conditions, with cholest-4-en-3-one as a substrate, the degradation of the substrate by the complementation strains was tested. A test result indicated that the ability of the gene knockout strains in degrading cholest-4-en-3-one was impeded, while the knocked-out gene complementation strains decreased such an impeding effect to a certain degree. The present invention proved in the end that the three enzymes SMO were key enzymes in the process of sterol degradation.

A specific construction method for the combinant strains was as follows:

(1) Cloning the Complete Sequence of a Steroid C27-Monooxygenase (SMO) Gene

According to the whole genome sequence (NC-023036) of *Mycobacterium neoaurum* VKM Ac-1815D published by the website GENBANK, three SMO genes (Smo1, Smo2, Smo3) were found out, and according to specific gene sequences, corresponding gene primers ere designed. With prepared *Mycobacterium neoaurum* chromosome DNA as a template, corresponding complete gene sequences were amplified out by PCR.

PCR reaction system: 5 µL of 10×ExTaq Buffer; 4 µL of dNTP; 1 µL of template DNA; 0.5 µL of upstream primer; 0.5 µL of downstream primer; 1 µL of ExTaq enzyme; and ddH$_2$O accounting for the rest of a total volume of 50 µL. PCR reaction condition: 94° C. 5 min; 94° C. 30 s; 65° C. 45 s; 72° C. 90 s; 35 times of cycling; 72° C. 10 min; and 12° C. 10 min.

Referring to the instructions of a gel extraction kit of Shanghai Generay Biotech Co., Ltd, a PCR product was recycled. The gel extraction product was connected to pMD18-T vector overnight according to a certain proportion, *E. coli* JM109 competent cells were transformed, an ampicillin resistant plate was utilized to screen recombinant bacteria, recombinant plasmids underwent restriction enzyme digestion to release gene bands, the sizes of which were about 2.7 kb and 1.3 kb, this indicated that recombinant plasmid construction was successful, and the recombinant plasmids were named as pMD18-T-Smo1, pMD18-T-Smo2 and pMD18-T-Smo3.

(2) Constructing *Mycobacterium neoaurum* Gene Knockout Plasmids

Specific primers were designed, and by way of PCR, 300 bp sequences were amplified out from the upstream of Smo1, Smo2 and Smo3 and 450 bp sequences were amplified out from the downstream. The gene sequences amplified from the upstream and the downstream were mixed as a template, and the upstream primers of the upstream 300 bp sequences and the downstream primers of the 450 bp sequences were utilized to amplify out 750 bp sequences. The amplified sequences and a knockout plasmid p2NIL underwent double-restriction enzyme (KpnI and Hind III) digestion, gel extraction and purification were conducted, T4 DNA ligase was connected to two segments overnight, conjugates underwent heat shock to transform *E. coli* JM109 competent cells after overnight, and a kanamycin resistant plate was utilized to screen positive transformants. Transformant plasmids were extracted, and the construction of recombinant plasmids was verified successful by restriction enzyme digestion. Single-restriction enzyme (Pac I) digestion was utilized to cut off a selectable marker gene cassette in a plasmid pGOAL19 and inserted it into the restriction enzyme (Pac I) digestion sites of the constructed recombinant plasmids, so that knockout plasmids p2N-ΔSmo1, p2N-ΔSmo2 and p2N-ΔSmo3 were constructed. The construction of the knockout plasmids was verified successful by PCR.

(3) Constructing *Mycobacterium neoaurum* Knocked-Out Gene Complementation Plasmids A plasmid pMV306 was used for the complementation of knocked-out genes. Double-restriction enzyme (Xba Ida I) digestion was utilized to cut off the corresponding gene segments in the recombinant plasmids p261-Smo1, p261-Smo2 and p261-Smo3 along with heat shock promoters hsp60 and connected them onto corresponding restriction enzyme (pMV306) digestion sites, so that knocked-out gene complementation plasmids p306-Smo1, p306-Smo2 and p306-Smo3 were constructed.

(4) Transforming the Recombinant Plasmids into the *Mycobacterium neoaurum* by an Electrotransformation Method A. The successfully constructed recombinant plasmids were transformed into the *Mycobacterium neoaurum* by using an electrotransformation method. The improved Gordhan and Parish method was adopted as the transformation method.

B. Positive transformants of the recombinant strains *M. neoaurum* were screened;

Colonies which grow out on plates with corresponding antibiotic pressures were chosen, flasks were shaken for fermentation, and the plasmids were extracted to be verified by restriction enzyme digestion.

Example 2: Construction of Recombinant Strains Intensively Expressing SMO

A plasmid pMV261 was utilized to overexpress the gene in *Mycobacterium neoaurum*. Sac I and Hind III were utilized to carry out double-restriction enzyme digestion on pMD18-T-Smo1, BamH I and EcoR I were utilized to respectively carry out double-restriction enzyme digestion on pMD18-T-Smo2 and pMD18-T-Smo3, meanwhile, a corresponding restriction enzyme digestion site was utilized to carry out restriction enzyme digestion on the plasmid pMV261, gel extraction and purification were carried out on the corresponding gene segments and the plasmid pMV261 segment, T$_4$ DNA ligase connected the two segments overnight, conjugates underwent heat shock to transform *E. coli* JM109 competent cells after overnight, and a kanamycin resistant plate was utilized to screen positive transformants. Transformant plasmids were extracted, the construction of recombinant plasmids p261-Smo1, p261-Smo2 and p261-Smo3 was verified successful by restriction enzyme digestion, the successfully constructed recombinant plasmids were electrotransformed respectively into *Mycobacterium neoaurum* JC-12 for the high yield of ADD (*Mycobacterium neoaurum* JC-12 had been disclosed by Shao M L, Zhang X, Rao Z M, Xu Mi, Yang T W, Li H, Xu Z H (2015) in the document of Enhanced production of androsta-1,4-diene-3,17-dione by *Mycobacterium neoaurum* JC-12 using three-stage fermentation strategy. PLoS ONE 10(9): e0137658), and thereby recombinant strains JC-12$_{S1}$, JC-12$_{S2}$ and JC-12$_{S3}$ were obtained respectively.

Example 3: Increase of ADD Yield by Recombinant Strains Intensively Expressing SMO After being activated in a seed medium, the recombinant strains JC-12$_{S1}$, JC-12$_{S2}$ and JC-12$_{S3}$ were inoculated into a fermentation medium according to an inoculation amount of 5%, fermentation was carried out with 20 g·L$^{-1}$ cholesterol as a substrate under the conditions of 30° C. and 160 rpm for 168 h, and a fermentative transformation experiment was conducted. The seed medium consisted of 10 g·L$^{-1}$ glucose, 10 g·L$^{-1}$ peptone, 6 g·L$^{-1}$ beef extract and 10 g·L$^{-1}$ NaCl, and pH was 7.5. The fermentation medium consisted of 20 g·L$^{-1}$ cholesterol, 20 g·L$^{-1}$ glucose, 10 g·L$^{-1}$ peptone, 6 g·L$^{-1}$ beef extract, 3 g·L$^{-1}$ K$_2$HPO$_4$, 0.5 g·L$^{-1}$ MgSO$_4$·7H$_2$O, 5×10−4 g·L$^{-1}$ MnCl$_2$.4H$_2$O and 60 g·L$^{-1}$ hydroxypropyl-β-cyclodextrin, and pH was 7.5.

The change of the ADD yield was detected. A result indicated that after 168 h of fermentative transformation, the ADD yield of the recombinant bacteria JC-12$_{S2}$ overexpressing SMO2 was increased most remarkably, and increased from 5.2 g·L$^{-1}$ *Mycobacterium neoaurum* JC-12 as the original strain to 7.3 g·L$^{-1}$. In addition, the ADD yields of the recombinant bacteria JC-12$_{S1}$ and JC-12$_{S3}$ were increased respectively to 6.5 g·L$^{-1}$ and 6.1 g·L$^{-1}$.

What is claimed is:

1. Recombinant *Mycobacterium neoaurum*
   wherein the recombinant *Mycobacterium neoaurum* overexpresses a steroid C27-monooxygenase gene;
   wherein the steroid C27-monooxygenase gene is a *Mycobacterium neoaurum* C27-monooxygenase gene selected from the group consisting of: *Mycobacterium neoaurum* Smo1 gene, *Mycobacterium neoaurum* Smo2 gene, and *Mycobacterium neoaurum* Smo3 gene
   wherein the amino acid sequences of the steroid C27-monooxygenase genes Smo1, Smo2, and Smo3 are SEQ ID NOS: 4, 5, and 6, respectively, and
   wherein the recombinant *Mycobacterium neoaurum* produces an increased yield of androsta-1,4-diene-3,17-dione (ADD) when fermented in the presence of cholesterol at 30° C. in fermentation medium that supports growth of *Mycobacterium neoaurum* compared to the yield of ADD produced by the *Mycobacterium neoaurum* lacking overexpression of the steroid C27-monooxygenase gene.

2. The recombinant *Mycobacterium neoaurum* according to claim 1, wherein the recombinant *Mycobacterium neoaurum* further comprises a recombinant plasmid comprising the steroid C27-monooxygenase gene.

3. A method for producing ADD which comprises;
   providing the recombinant *Mycobacterium neoaurum* of claim 1 as a production strain; and
   incubating the recombinant *Mycobacterium neoaurum* with phytosterol or cholesterol or both under conditions that support overexpression of the steroid C27-monooxygenase gene in the recombinant *Mycobacterium neoaurum*.

* * * * *